US00RE48201E

(19) United States
(12) Reissued Patent
Nackashi et al.

(10) Patent Number: US RE48,201 E
(45) Date of Reissued Patent: Sep. 8, 2020

(54) SPECIMEN HOLDER USED FOR MOUNTING SAMPLES IN ELECTRON MICROSCOPES

(71) Applicant: Protochips, Inc., Morrisville, NC (US)

(72) Inventors: David P. Nackashi, Raleigh, NC (US); John Damiano, Apex, NC (US); Stephen E. Mick, Weimar, TX (US); Thomas G. Schmelzer, Cranberry Township, PA (US); Michael Zapata, Cary, NC (US)

(73) Assignee: Protochips, Inc., Morrisville, NC (US)

(21) Appl. No.: 15/291,894

(22) Filed: Oct. 12, 2016

Related U.S. Patent Documents

Reissue of:
(64) Patent No.: 8,859,991
Issued: Oct. 14, 2014
Appl. No.: 13/799,871
Filed: Mar. 13, 2013

U.S. Applications:
(62) Division of application No. 12/933,213, filed as application No. PCT/US2009/037396 on Mar. 17, 2009, now Pat. No. 8,513,621.

(60) Provisional application No. 61/085,650, filed on Aug. 1, 2008, provisional application No. 61/037,115, filed on Mar. 17, 2008.

(51) Int. Cl.
*E04H 4/08* (2006.01)
*H01J 37/20* (2006.01)
*G01N 1/28* (2006.01)

(52) U.S. Cl.
CPC ..... *E04H 4/082* (2013.01); *G01N 1/28* (2013.01); *H01J 37/20* (2013.01); *H01J 2237/2008* (2013.01)

(58) Field of Classification Search
CPC ..... H01J 37/20; H01J 2237/2008; H01J 2237/2007; G01N 1/28
USPC ..... 250/440.11, 306, 307
See application file for complete search history.

(56) References Cited

U.S. PATENT DOCUMENTS

| | | | | |
|---|---|---|---|---|
| 4,520,776 | A | 6/1985 | Ishida et al. | |
| 4,620,776 | A * | 11/1986 | Ima | 359/391 |
| 4,672,797 | A * | 6/1987 | Hagler | 53/467 |
| 4,833,330 | A * | 5/1989 | Swann et al. | 250/443.1 |
| 4,996,433 | A * | 2/1991 | Jones et al. | 250/443.1 |
| 5,089,708 | A * | 2/1992 | Asselbergs | 250/442.11 |
| 5,096,550 | A * | 3/1992 | Mayer et al. | 205/642 |

(Continued)

FOREIGN PATENT DOCUMENTS

| | | | | |
|---|---|---|---|---|
| DE | 19533216 A1 * | 3/1997 | | H01J 37/20 |
| DE | 19533216 C2 * | 1/1998 | | |

(Continued)

OTHER PUBLICATIONS

Japanese Patent Office, Office Action and English Translation, Japanese Patent Application No. 2011-500896, dated Sep. 2, 2013.

(Continued)

*Primary Examiner* — Albert J Gagliardi
(74) *Attorney, Agent, or Firm* — NK Patent Law

(57) ABSTRACT

A novel specimen holder for specimen support devices for insertion in electron microscopes. The novel specimen holder of the invention provides mechanical support for specimen support devices and as well as electrical contacts to the specimens or specimen support devices.

19 Claims, 16 Drawing Sheets

(56) References Cited

U.S. PATENT DOCUMENTS

| | | | | |
|---|---|---|---|---|
| 5,124,645 | A * | 6/1992 | Rhoden et al. | 324/754.22 |
| 5,225,683 | A * | 7/1993 | Suzuki et al. | 250/442.11 |
| 5,367,171 | A * | 11/1994 | Aoyama et al. | 250/443.1 |
| 5,406,087 | A * | 4/1995 | Fujiyoshi et al. | 250/440.11 |
| 5,412,180 | A * | 5/1995 | Coombs, III | 219/385 |
| 5,438,254 | A | 8/1995 | Ho et al. | |
| 5,464,977 | A * | 11/1995 | Nakagiri et al. | 250/234 |
| 5,698,856 | A * | 12/1997 | Frasca | 250/440.11 |
| 6,300,124 | B1 * | 10/2001 | Blumenfeld et al. | 435/287.2 |
| 6,495,838 | B1 * | 12/2002 | Yaguchi et al. | 250/443.1 |
| 6,538,254 | B1 * | 3/2003 | Tomimatsu et al. | 250/442.11 |
| 6,657,431 | B2 * | 12/2003 | Xiao | 324/244 |
| 6,809,533 | B1 * | 10/2004 | Anlage et al. | 324/244 |
| 6,828,566 | B2 * | 12/2004 | Tomimatsu et al. | 250/442.11 |
| 7,071,475 | B2 * | 7/2006 | Tomimatsu et al. | 250/442.11 |
| 7,132,673 | B2 * | 11/2006 | Fischione et al. | 250/492.3 |
| 7,138,628 | B2 * | 11/2006 | Tomimatsu et al. | 250/306 |
| 7,145,330 | B2 * | 12/2006 | Xiao | 324/244 |
| 7,176,458 | B2 * | 2/2007 | Tomimatsu et al. | 250/306 |
| 7,381,968 | B2 * | 6/2008 | Tanaka et al. | 250/440.11 |
| 7,397,050 | B2 * | 7/2008 | Tomimatsu et al. | 250/492.21 |
| 7,397,052 | B2 * | 7/2008 | Tomimatsu et al. | 250/492.21 |
| 7,504,623 | B2 * | 3/2009 | Fischione et al. | 250/309 |
| 7,525,108 | B2 * | 4/2009 | Tomimatsu et al. | 250/492.21 |
| 7,798,011 | B2 * | 9/2010 | Warren et al. | 73/780 |
| 8,334,519 | B2 * | 12/2012 | Ono et al. | 250/440.11 |
| 2002/0033695 | A1 * | 3/2002 | Xiao | 324/244 |
| 2003/0183776 | A1 * | 10/2003 | Tomimatsu et al. | 250/442.11 |
| 2004/0003666 | A1 * | 1/2004 | Fischione et al. | 73/856 |
| 2004/0207396 | A1 * | 10/2004 | Xiao | 324/244 |
| 2005/0054029 | A1 * | 3/2005 | Tomimatsu et al. | 435/40.5 |
| 2005/0230636 | A1 * | 10/2005 | Tanaka et al. | 250/440.11 |
| 2006/0022148 | A1 * | 2/2006 | Fischione et al. | 250/492.21 |
| 2006/0025002 | A1 * | 2/2006 | Zhang et al. | 439/329 |
| 2006/0097187 | A1 | 5/2006 | Zandbergen | |
| 2006/0192099 | A1 * | 8/2006 | Tomimatsu et al. | 250/281 |
| 2006/0231776 | A1 * | 10/2006 | Tomimatsu et al. | 250/492.21 |
| 2007/0023701 | A1 * | 2/2007 | Fishione et al. | 250/492.21 |
| 2007/0116600 | A1 * | 5/2007 | Kochar et al. | 422/65 |
| 2007/0145299 | A1 * | 6/2007 | Tomimatsu et al. | 250/492.21 |
| 2007/0145300 | A1 * | 6/2007 | Tomimatsu et al. | 250/492.21 |
| 2007/0145302 | A1 * | 6/2007 | Tomimatsu et al. | 250/492.21 |
| 2007/0180924 | A1 * | 8/2007 | Warren et al. | 73/780 |
| 2008/0067374 | A1 * | 3/2008 | Ono et al. | 250/310 |
| 2008/0308727 | A1 * | 12/2008 | Boguslavsky et al. | 250/307 |

FOREIGN PATENT DOCUMENTS

| | | | |
|---|---|---|---|
| EP | 1939923 | A2 | 7/2008 |
| JP | S50024072 | A | 3/1975 |
| JP | S60164761 | U | 11/1985 |
| JP | 7128206 | A | 5/1995 |
| WO | 2008141147 | A1 | 11/2008 |

OTHER PUBLICATIONS

Zhang, M., et al.; "In situ transmission electron microscopy studies enabled by microelectromechanical system technology," Journal of Materials Research, 2005, Pgs. 1802-1807, vol. 20.

EPO, Supplementary European Search Report, European Application No. 09722296.2, dated Mar. 8, 2012.

Zhang, Xiao, et al.; "A Simple Specimen Holder for EBIC Imaging on the Hitachi S800," Microscopy Research and Technique, 1993, pp. 182-183, vol. 26.

* cited by examiner

SPECIMEN HOLDER USED FOR MOUNTING SAMPLES IN ELECTRON MICROSCOPES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is filed under the provisions of 35 U.S.C. §111(a) and is a continuation of U.S. patent application Ser. No. 12/933,213 filed on Feb. 9, 2011, which claims priority to International Patent Application No. PCT/US2009/037396 filed on 17 Mar. 2009 entitled "Specimen Holder Used for Mounting Samples in Electron Microscopes" in the name of David P. Nackashi, et al., which claims priority of U.S. Provisional Patent Application Nos. 61/037,115 filed on 17 Mar. 2008 and 61/085,650 filed on 1 Aug. 2008, all of which are hereby incorporated by reference herein in their entirety. This application is also co-pending with U.S. patent application Ser. No. 13/758,829 filed on Feb. 4, 2013.

FIELD

The invention relates generally to specimen holders used for mounting samples in an electron microscope, e.g., a transmission electron microscope (TEM), a scanning transmission electron microscopy (STEM) and variations of the scanning electron microscopes (SEM) that use traditional TEM-type holders and stages.

BACKGROUND

The specimen holder is a component of an electron microscope providing the physical support for specimens under observation. Specimen holders traditionally used for TEMs and STEMs, as well as some modern SEMs, consist of a rod that is comprised of three key regions: the end, the barrel and the specimen tip (see, e.g., FIG. 1). In addition to supporting the specimen, the specimen holder provides an interface between the inside of the instrument (i.e., a vacuum environment) and the outside world.

To use the specimen holder, one or more samples are first placed on a support device. The support device is then mechanically fixed in place at the specimen tip, and the specimen holder is inserted into the electron microscope through a load-lock. During insertion, the specimen holder is pushed into the electron microscope until it stops, which results in the specimen tip of the specimen holder being located in the column of the microscope. At this point, the barrel of the specimen holder bridges the space between the inside of the microscope and the outside of the load lock, and the end of the specimen holder is outside the microscope. To maintain an ultra-high vacuum environment inside the electron microscope, flexible o-rings are typically found along the barrel of the specimen holder, and these o-rings seal against the microscope when the specimen holder is inserted. The exact shape and size of the specimen holder varies with the type and manufacturer of the electron microscope, but each holder contains these three key regions.

Interfacing semiconductor-based devices with specimen holders for use in electron microscopes has seen limited commercial development. There are, however, a few applications that have either required an electrical interface between the sample and the specimen holder, or have incorporated semiconductor devices in a research environment.

Several electron microscopy techniques, including Electron Beam Induced Current (EBIC), require an electrical contact between a sample and the specimen holder itself. Typically, this is done using a simple screw and metallic clip, which is gently pressed down onto the sample by tightening the screw (see, X. Zhang and D. Joy, "A simple specimen holder for EBIC imaging on the Hitachi S800," J. Microscopy Res. and Techn., Vol. 26(2), pp. 182-183, 1993). A wire is either soldered to the clip or looped around the screw head to provide an electrical path from the sample, through the clip, and to the specimen holder which routes the wire outside of the instrument. This approach is tedious, requiring the user to manually align the clips over the appropriate regions on the device, then manually tighten every screw that is needed to complete an electrical path to the specimen holder. Because of the small size of these screws and the sample itself, this approach takes time and requires a substantial amount of dexterity.

An alternative approach (U.S. Pat. No. 5,124,645) requires a wirebond, or solder joint, to establish a more durable connection between the sample and the specimen tip of a specimen holder. These connections, however, are permanent and do not allow samples to be easily interchanged between experiments. Following an experiment, to exchange samples, the specimen holder must be placed back into a wirebond machine or soldering must again be performed to create a new electrical connection with the new sample. This approach is tedious, requires great dexterity, and is likely to damage the specimen tip after repeated use.

An approach developed at the University of Illinois (U.S. patent application Ser. No. 11/192,300) addresses some of these concerns. This approach allows a semiconductor device to be mounted in a specimen tip, making as many as twelve simultaneous electrical connections between the holder and the device. A frame (generally U-shaped) aligns the device and baseplate with electrical spring contact fingers and provides a rigid surface against which the device is pressed, providing stability and forming electrical contacts between the device and the specimen holder. The baseplate is the component of the specimen tip that provides a stable surface upon which the device can be mounted, and contains electrical spring contact fingers in complementary positions to the device, which when aligned using the frame, make contacts simultaneously between the baseplate and the device. Disadvantageously, spring contact fingers such as these are delicate and more difficult to manufacture. Removing the device from the baseplate completely exposes the spring clips and presents an opportunity to accidentally bend or break these fingers, compromising the electrical connections.

Considering the disadvantages of the prior art, a novel specimen holder is needed, wherein said specimen holder eliminates the need for delicate spring contact fingers and provides a simple method for repeatedly mounting and exchanging devices without disassembly or soldering.

SUMMARY

The present invention relates generally to a novel specimen holder which provides mechanical support for specimen support devices and as well as electrical contacts to the specimens or specimen support devices.

In one aspect, an electron microscope specimen holder is described, said specimen holder comprising a body, a clipping means, and at least one guide mechanism. The specimen holder may further comprise a spring or a spring cantilever.

In another aspect, an electron microscope specimen holder is described, said specimen holder comprising a body, a clipping means, and at least one guide mechanism, wherein the clipping means comprise an article of manufacture having a top surface, a bottom surface, a first end, a securing means, a second end, and at least one electrical contact integrated on and/or in the bottom surface of the article. The securing means may comprise one of a pivot positioned between the first end and the second end of the article; a fixed point at or near the first end of the article and wherein the article is flexible; or a set screw. The specimen holder may further comprise a spring or a spring cantilever.

In each of these aspects, the specimen holder may further comprise a specimen support device mechanically secured between the clipping means and the body. The specimen support device may comprise a frame, at least one electrical lead and at least one membrane region.

In still another aspect, a method of providing an electrical contact between a specimen and a specimen holder of an electron microscope is described, said method comprising:

positioning a specimen on a specimen support device, wherein the specimen support device comprises a frame, at least one electrical lead and at least one membrane region; and inserting the specimen support device in a specimen holder, wherein the specimen holder comprises a body, a clipping means, and at least one guide mechanism, wherein the clipping means comprise at least one electrical contact integrated on and/or in a bottom surface of the clipping means; and wherein at least one electrical lead of the device substantially contacts at least one electrical contact of the clipping means.

Yet another aspect relates to a method of using a specimen holder in electron microscopy, said method comprising:

positioning a specimen support device in a specimen holder as described herein; and inserting said specimen holder in an electron microscope.

Other aspects, features and advantages of the invention will be more fully apparent from the ensuing disclosure and appended claims.

DETAILED DESCRIPTION

Figure 1:
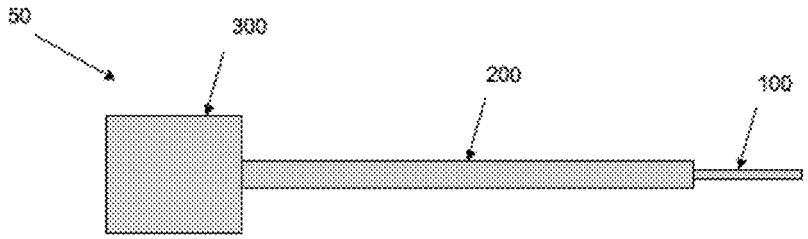
FIG. 1 shows a schematic of a generic specimen holder (50). The specimen holder is comprised of three regions: the tip (100), the barrel (200), and the end (300).

The present invention generally relates to novel specimen holders, methods for interfacing samples at the tip of the specimen holder, and uses of the novel specimen holder. It is to be understood that the specimen holder and specimen holder interface described herein are compatible with and may be interfaced with the semiconductor specimen support devices disclosed in U.S. patent application Ser. Nos. 60/916,916 and 60/974,384, which are incorporated herein by reference in their entirities. It should be appreciated by one skilled in the art that alternative specimen support devices may be interfaced with the specimen holder described herein. The specimen holder provides mechanical support for one or more specimens or specimen support devices and may also provide electrical contacts to the specimens or specimen support devices. The specimen holder can be manufactured with tips, barrels and ends of various shapes and sizes such that the specimen holder fits any manufacturer's electron microscope.

As defined herein, a "spring" corresponds to any object that has a spring constant (k) and which exerts a force onto the specimen support device when it is loaded in the specimen holder. The spring may or may not observe Hooke's law (F=−kx) depending on the material of construction.

As defined herein, a "hinge" connects two solid objects, in the present case the insulating clip and the mounting surface, typically allowing only a limited angle of rotation between them. Two objects connected by a hinge rotate relative to each other about a fixed axis of rotation. It is also contemplated herein that the "hinge" may be one or two fulcrums attached to the mounting surface, wherein the clip is flexible.

As defined herein, a "membrane region" corresponds to unsupported material comprised, consisting of, or consisting essentially of carbon, silicon nitride, SiC or other thin films generally 1 micron or less having a low tensile stress (<500 MPa), and providing a region at least partially electron transparent region for supporting the at least one specimen. The membrane region may include holes or be hole-free. The membrane region may be comprised of a single material or a layer of more than one material and may be either uniformly flat or contain regions with varying thicknesses.

The present application improves on the prior art in several ways: (1) by eliminating the required use of a delicate spring contact finger, (2) by providing a method for accommodating semiconductor devices that are of various shapes and sizes without the need to machine frames and custom parts to align different devices geometries, and (3) by providing a simple method for mounting and exchanging devices and making electrical contacts to devices without the need for partially disassembling the specimen tip (e.g., removing screws or other small parts).

More specifically, rather than using spring contact fingers (bent slightly at their tips) to separately promote contact with each pad on the device, the specimen holder described herein includes at least one electrode placed on the bottom of an insulating clip, wherein the insulating clip with integrated electrode(s) provides simultaneous mechanical force to all electrodes, simultaneously presses the electrode(s) against contact pads on the device and provides mechanical force for securing the device in place for imaging. Clips and springs used in this application separately provide the mechanical force required to stabilize the device to the specimen holder, and are not used for electrical contacts between the device and the holder. Preferably, the springs are distally positioned along the insulating clip relative to the electrical contacts. This allows the electrical contacts on the clips to be manufactured using planar processes such as, but not limited to, precision machining, lithographic and/or electroplating processes.

Using the specimen holder described herein, only one side of the device is required to have contact pads matching the electrode pitch and width in order to line up with the electrodes underneath the clip. This design improves upon prior art in that it allows a variety of device lengths and shapes to be mounted into the specimen tip. This specimen holder also allows a device to be mounted quickly and easily, making both physical and electrical contacts, without the need to partially disassemble the specimen tip to mount the device.

Figure 2A:
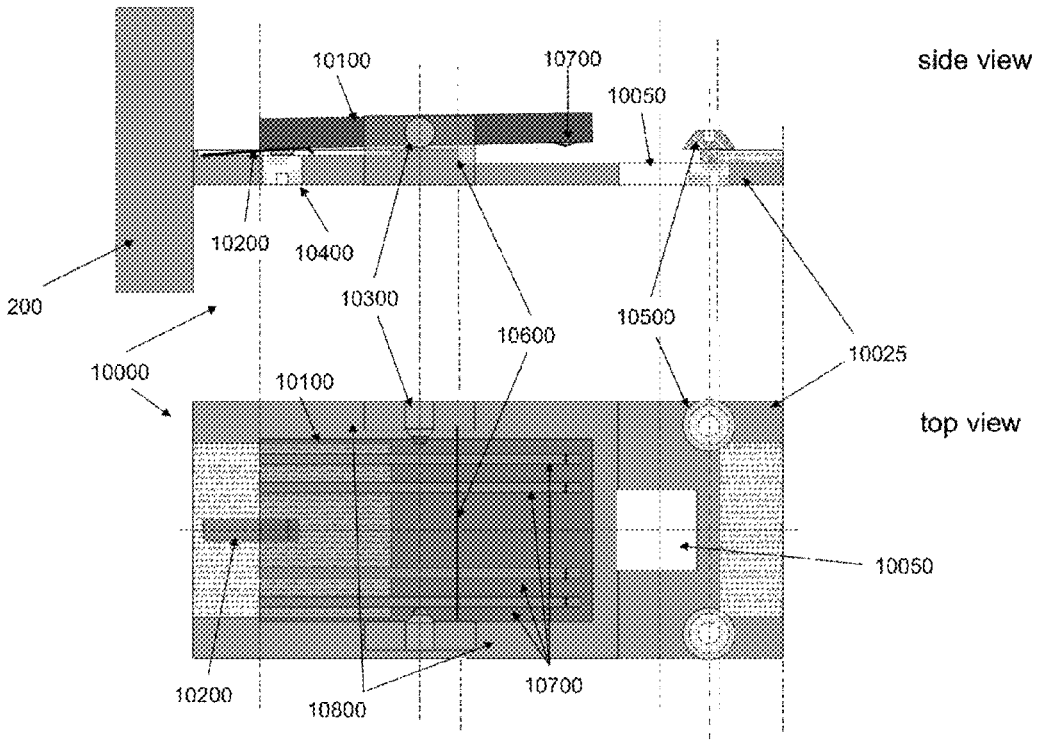
FIG. 2A shows one embodiment of the tip region of a specimen holder described herein wherein the holder tip (10000) shows a clamping mechanism in an open state ready to receive a specimen support device.
Figure 2B:
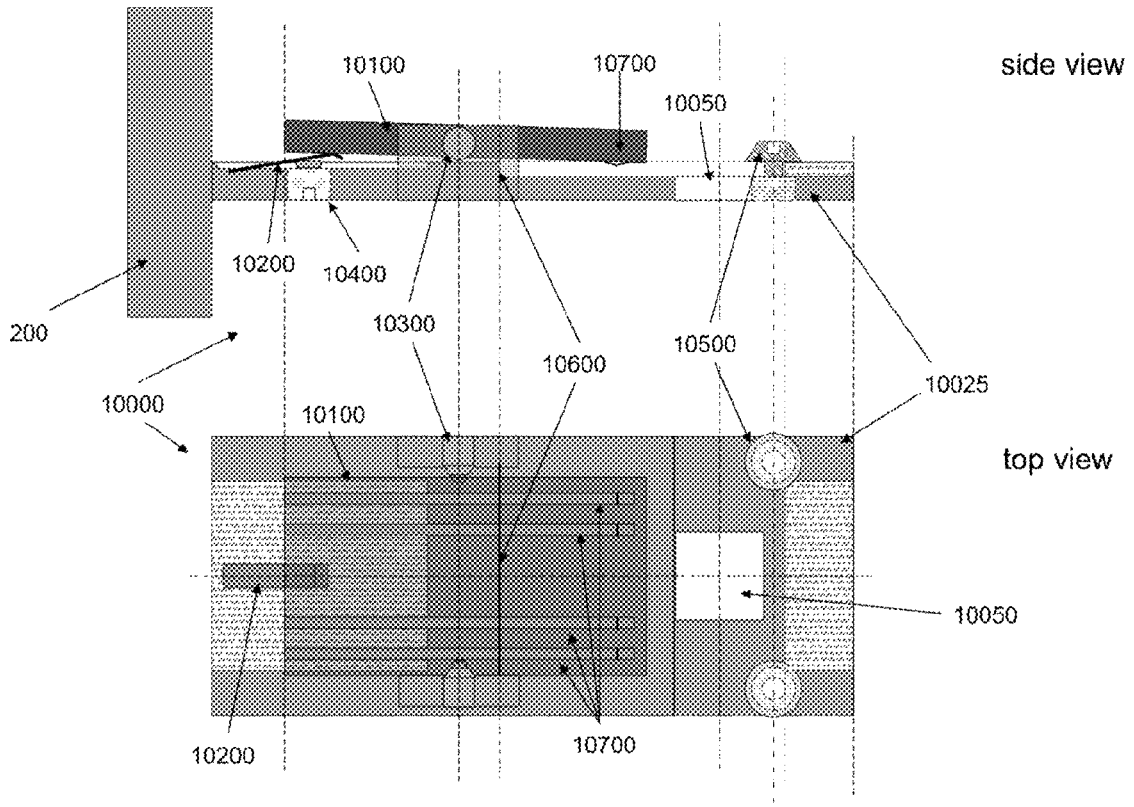
FIG. 2B shows one embodiment of the tip region of a specimen holder described herein wherein the holder tip (10000) shows a clamping mechanism in a closed state without a specimen support device.
Figure 2C:
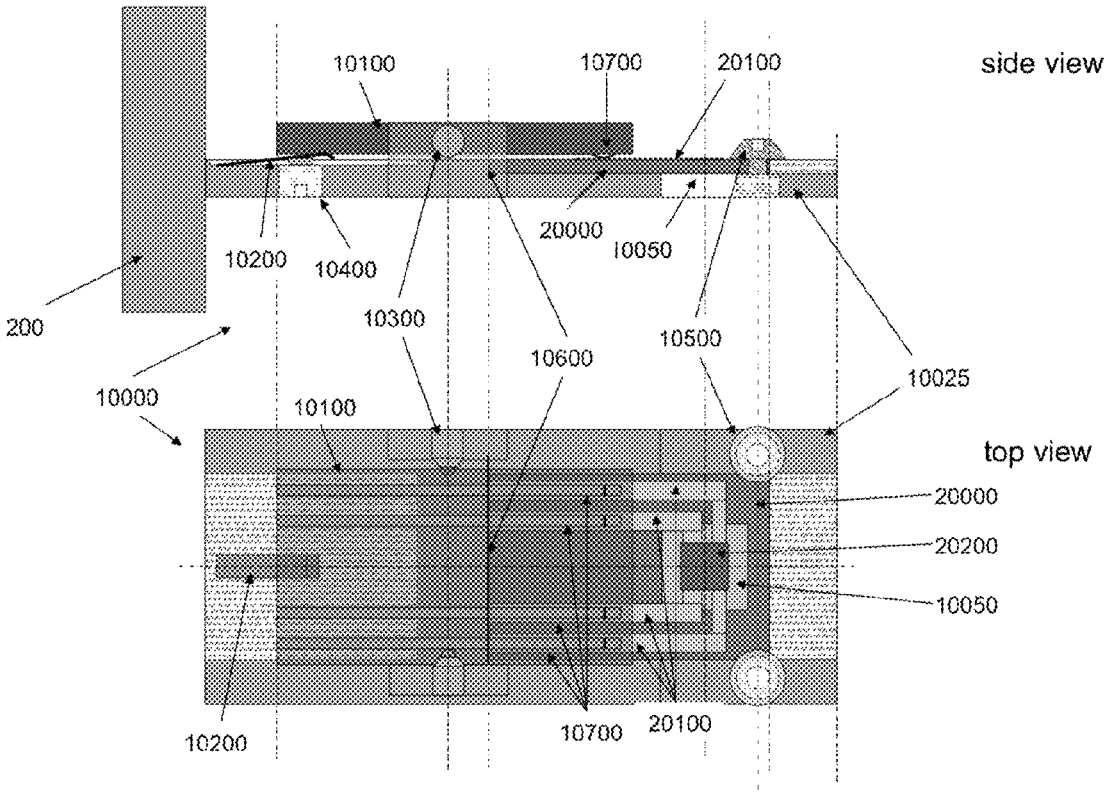
FIG. 2C shows one embodiment of the tip region of a specimen holder described herein wherein the holder tip (10000) shows a clamping mechanism in a closed state with a specimen support device.

One embodiment of the tip region of a specimen holder is shown is FIGS. 2A, 2B and 2C. FIG. 2A shows the tip region of a specimen holder wherein the holder tip (10000) includes a clamping mechanism in an open state ready to receive a specimen support device. FIG. 2B shows the tip region of the specimen holder of FIG. 2A wherein the holder tip (10000) is in a closed state without a specimen support device. FIG. 2C shows the tip region of the specimen holder of FIG. 2A wherein the holder tip (10000) is in an closed state with a specimen support device. In each of these figures, the clamping mechanism is comprised of a clip (10100), spring (10200), hinges (10300), set screw (10400), guide mechanism (10500), depth stop (10600), and at least one electrical contact (10700). The holder tip is comprised of a body (10025), a viewing region (10050), and the clamping mechanism. In FIG. 2C a device is loaded into the tip and held in place by the clamping mechanism. The device is generally comprised of a frame (20000), electrical leads (20100), and a membrane region (20200).

In the clamping mechanism, the clip (10100) acts as a lever, the spring (10200) provides constant tension to the clip, the hinges (10300) allow the clip to pivot about the hinge, the set screw (10400) prevents the spring (10200) from being over-compressed when a device is loaded, and the guide mechanism (10500), such as guide screws, guide pins, or guide posts, provides lateral alignment to a device as it is loaded. When a device is completely loaded, the depth stop (10600) provides a means both to align the electrical contacts of the specimen holder (10700) to electrical leads of a device (20100) and to align the viewing region of the specimen holder tip (10050) with the membrane region of a device (20200). It should be appreciated by one skilled in the art that the electrical contacts of the specimen holder (10700) may extend from one length of the clip to the other or may be present in shorter sections so long as the electrical contacts are present for contact with the electrical leads of the device (20100).

The resting position for the clamping mechanism is shown in FIG. 2B where a spring (10200) pushes upward at one end of the clip (10100), resulting in downward pressure created at the opposite end of the clip where the clip pivots at a set of hinges (10300). The hinge is mounted to a planar mounting surface (10800), said mounting surface extending from the barrel to at least the end of the clip and possibly further. When this mounting surface extends beyond the clip, a viewing region (10050) will typically be included therein just beyond the clip.

To mount the device, downward pressure is placed on the spring end of the clip, which lifts the opposite end above the surface to a level at least as high as the thickness of the device, and typically higher, for example, greater than 1 mm (see FIG. 2A), although less than 1 mm is contemplated. The device is either placed in between the clip and the mounting surface manually, or slid underneath the clip along the mounting surface using the guide screws and depth stop as guidance. Once the device is in position, the pressure on the spring is released and the device is secured manually to the specimen tip (see FIG. 2C).

Electrical contacts from the holder to the device, typically in a range from 2 to 12 electrical contacts (10700), may be provided by the integrated conducting wires or paths underneath the clip. These electrical contacts are electrically isolated from each other and from the clip itself (if the clip is made of a conductive material). When electrical pads exist on the device, the guide mechanism and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will extend from the clip to the barrel, down the barrel to the end, and to a connector that exists at the specimen holder end that can be mated with a plug outside the microscope and connected to a power supply to provide voltage or current through the holder and interface to the specimen support device. Each conductor will remain isolated from each other as well as the three components of the specimen holder.

Figure 3A:
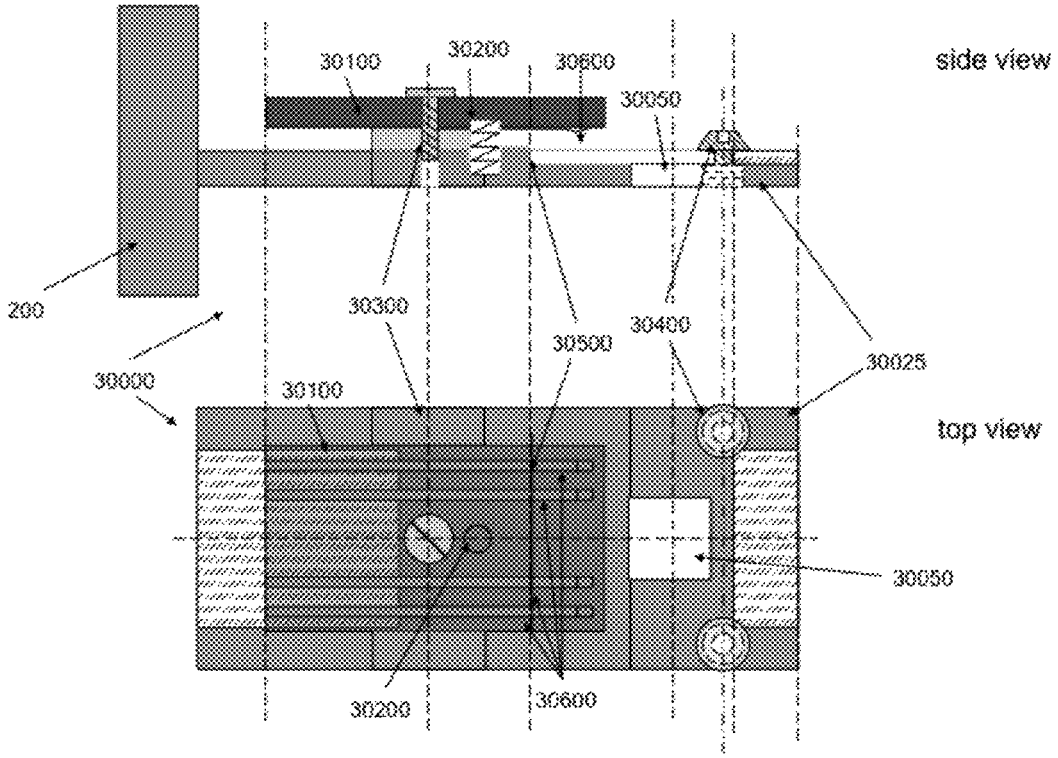
FIG. 3A shows a second embodiment of the tip region of a specimen holder described herein wherein the holder tip (30000) shows a clamping mechanism in an open state ready to receive a specimen support device.
Figure 3B:
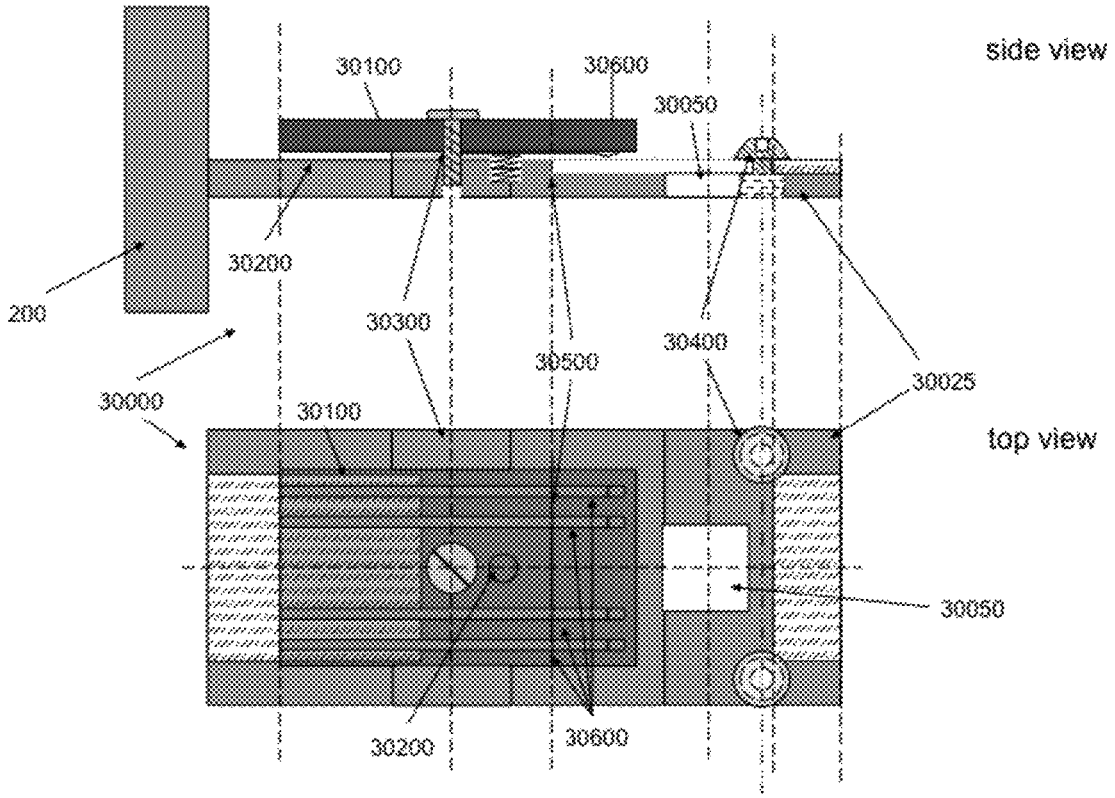
FIG. 3B shows a second embodiment of the tip region of a specimen holder described herein wherein the holder tip (30000) shows a clamping mechanism in a closed state without a specimen support device.
Figure 3C:
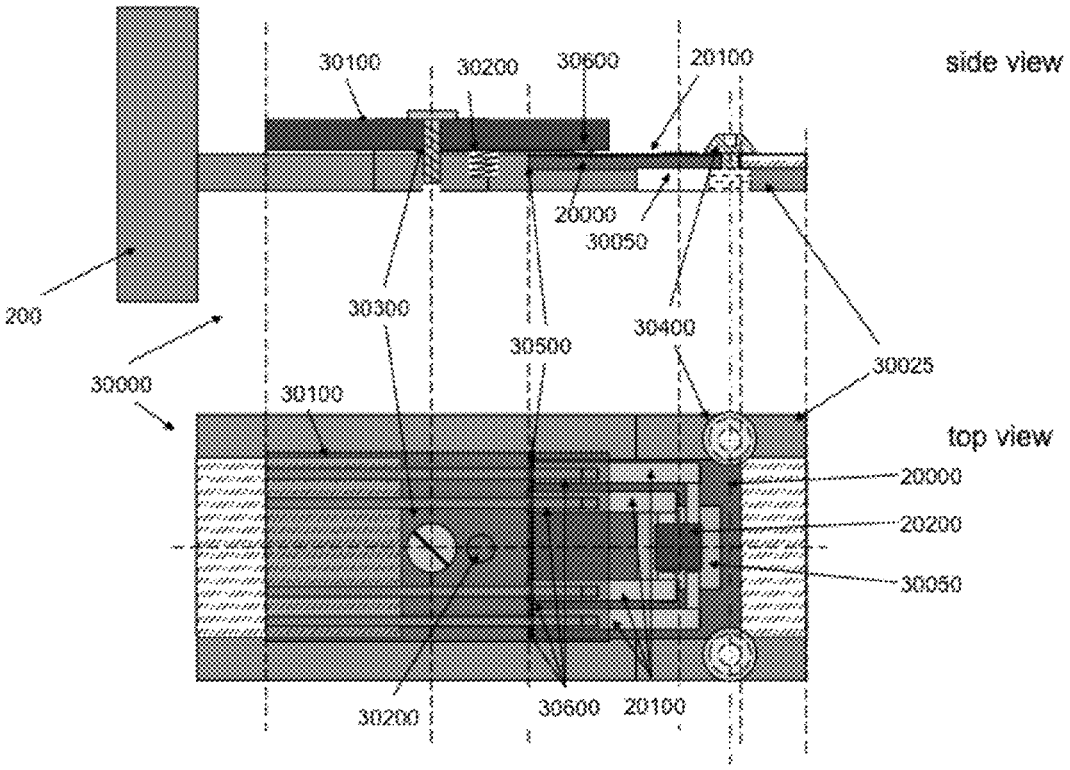
FIG. 3C shows a second embodiment of the tip region of a specimen holder described herein wherein the holder tip (30000) shows a clamping mechanism in an closed state with a specimen support device.

Another embodiment of the tip region of a specimen holder is shown in FIGS. 3A, 3B, and 3C. FIG. 3A shows the tip region of a specimen holder of the present invention where the holder tip (30000) includes a clamping mechanism in an open state ready to receive a specimen support device. FIG. 3B shows the tip region of the specimen holder of FIG. 3A where the holder tip (30000) is in a closed state without a specimen support device. FIG. 3C shows the tip region of the specimen holder of FIG. 3A where the holder tip (30000) is in a closed state with a specimen support device. In each of these figures, the clamping mechanism is comprised of a clip (30100), spring (30200), locking screw (30300), guide mechanism (30400), depth stop (30500), and at least one electrical contact (30600). The holder tip is comprised of a body (30025), a viewing region (30050), and the clamping mechanism. In FIG. 3C a device is loaded into the tip and held in place by the clamping mechanism. The device is generally comprised of a frame (20000), electrical leads (20100), and a membrane region (20200).

In the clamping mechanism, the clip (30100) acts as a clamp, the spring (30200) provides constant tension to the clip, the locking screw (30300) allows the clip to move up and down parallel to the plane of the body (30025), the guide mechanism (30400), such as guide screws, guide pins, or guide posts, provide lateral alignment to a device as it is loaded. When a device is completely loaded, the depth stop (30500) provides a means both to align the electrical contacts of the specimen holder (30600) to electrical leads of a device (20100) and to align the viewing region of the specimen holder tip (30050) with the membrane region of a device (20200). It should be appreciated by one skilled in the art that the electrical contacts of the specimen holder (30600) may extend from one length of the clip to the other or may be present in shorter sections so long as the electrical contacts are present for contact with the electrical leads of the device (20100).

The open position for the clamping mechanism is shown in FIG. 3B where a spring (30200) pushes upward at one end of the clip (30100), resulting in downward pressure pushing at the opposite end of the clip. The clip can be raised or lowered by a locking screw (30300) and when raised, the force exerted by the spring is enough to ensure that the front of the clip is raised enough to allow a specimen support device to be loaded into the holder.

To mount the device, the locking screw is turned to raise the clip to a level at least as high as the thickness of the device, and typically higher, e.g., greater than 1 mm (see FIG. 3A), although less than 1 mm is contemplated. The device is either placed in between the clip and the surface manually, or slid underneath the clip along the surface using the guide screws and depth stop as guidance. Once the device is in position, the locking screw is turned to lower the clip so that the clip secures the device to the specimen tip (see FIG. 3C).

Electrical contacts from the holder to the device, typically in a range from 2 to 12 electrical contacts (30600), may be provided by the integrated conducting wires or paths underneath the clip. These electrical contacts are electrically isolated from each other and from the clip itself (if the clip is made of a conductive material). When electrical pads exist on the device, the guide screws and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will extend from the clip to the barrel, down the barrel to the end, and to a connector that exists at the specimen holder end that can be mated with a plug outside the microscope and connected to a power supply. Each conductor will remain isolated from each other as well as the three components of the specimen holder.

Figure 4A:
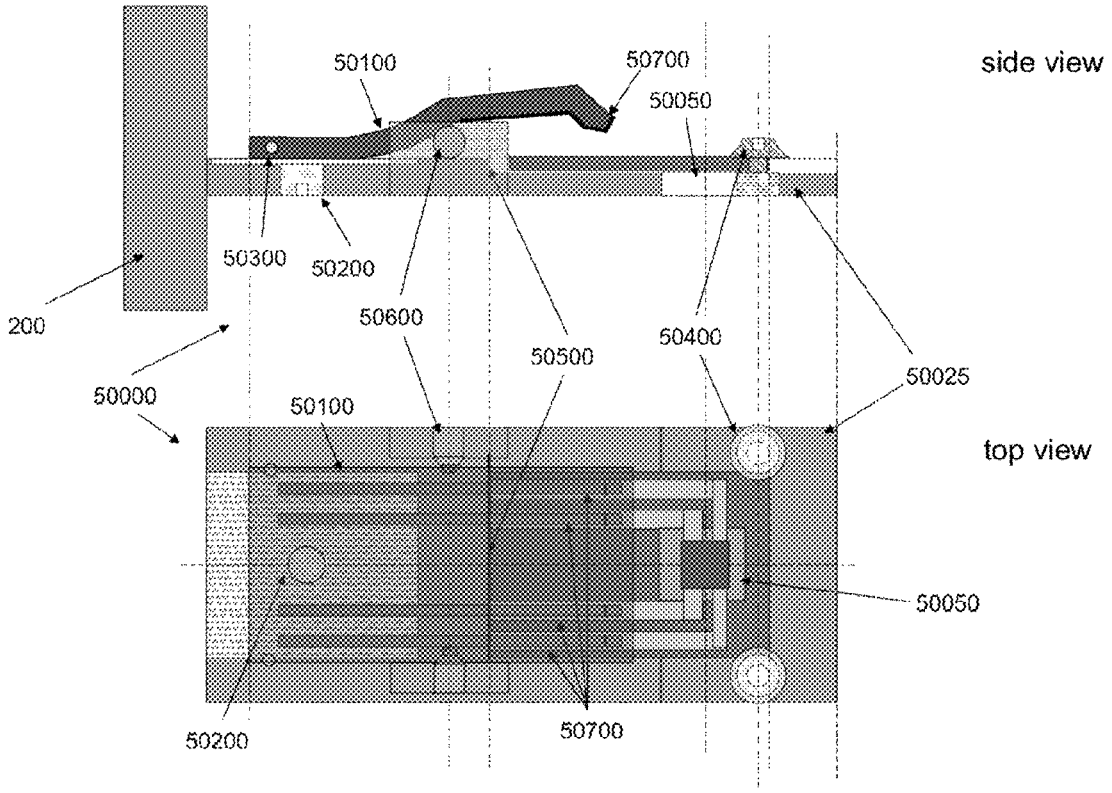
FIG. 4A shows a third embodiment of the tip region of a specimen holder described herein wherein the holder tip (50000) shows a flexing mechanism ready to receive a specimen support device, wherein the fulcrum is a two-piece fulcrum.
Figure 4B:
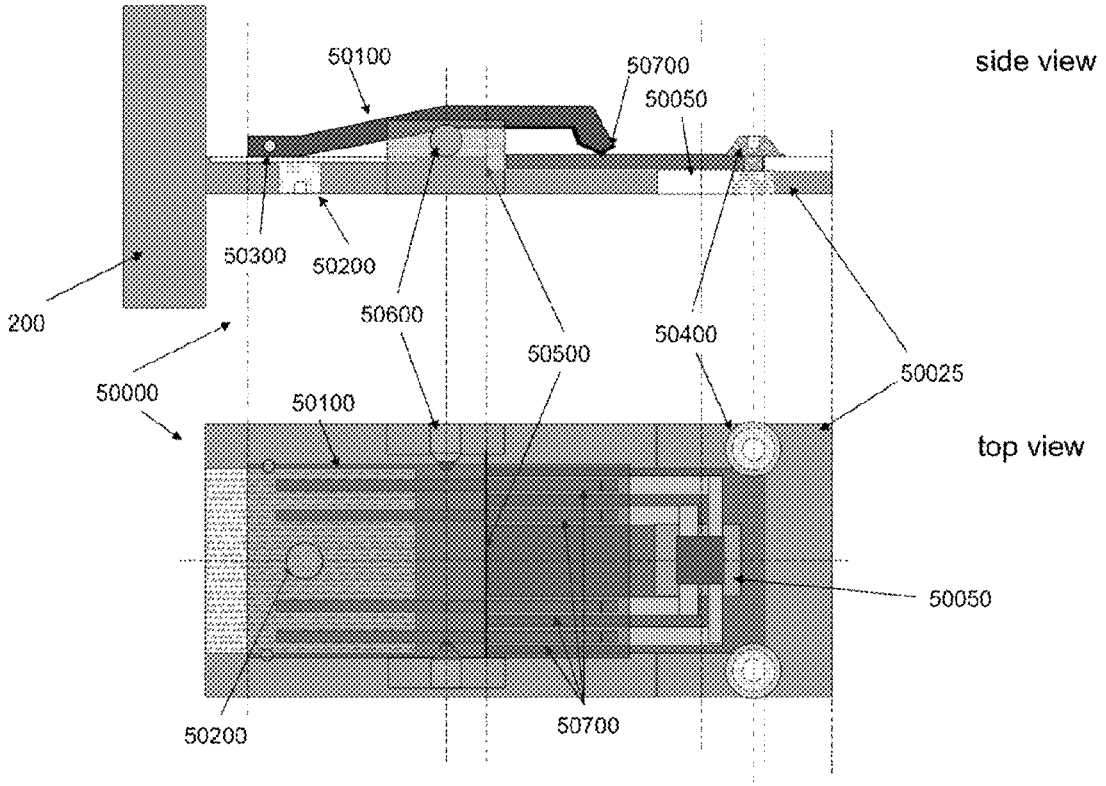
FIG. 4B shows a third embodiment of the tip region of a specimen holder described herein wherein the holder tip (50000) shows a flexing mechanism with a specimen support device, wherein the fulcrum is a two-piece fulcrum.
Figure 5A:
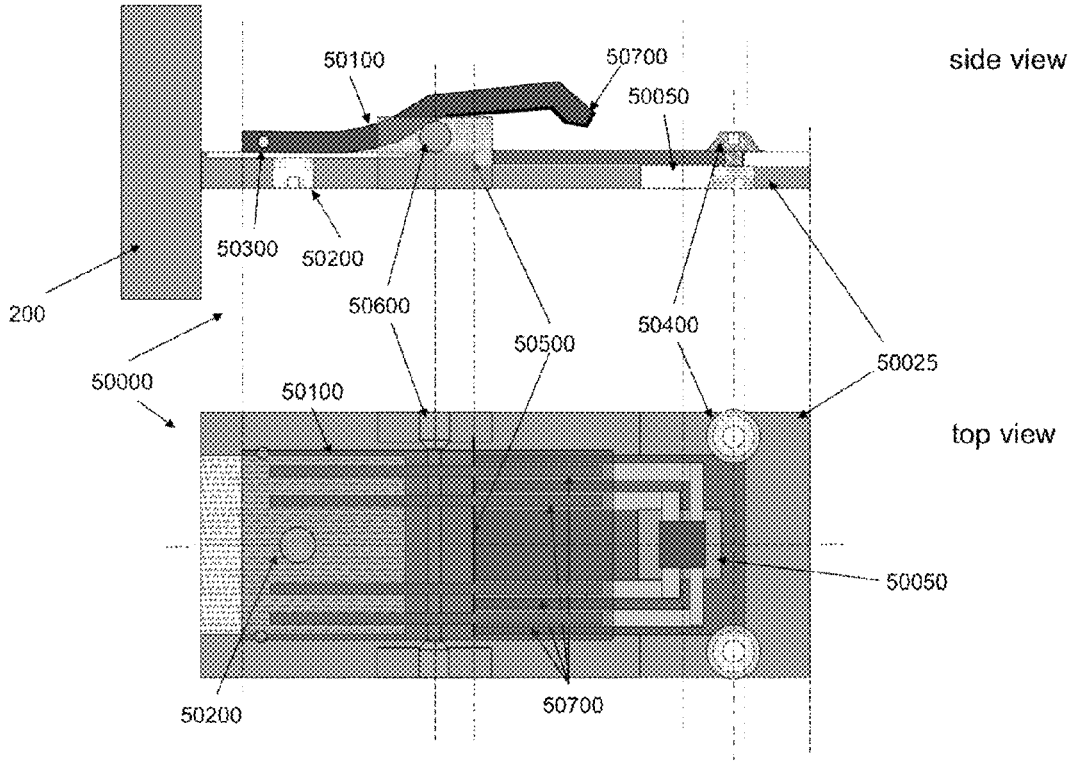
FIG. 5A shows a fourth embodiment of the tip region of a specimen holder described herein wherein the holder tip (50000) shows a flexing mechanism ready to receive a specimen support device, wherein the fulcrum is a one-piece fulcrum.
Figure 5B:
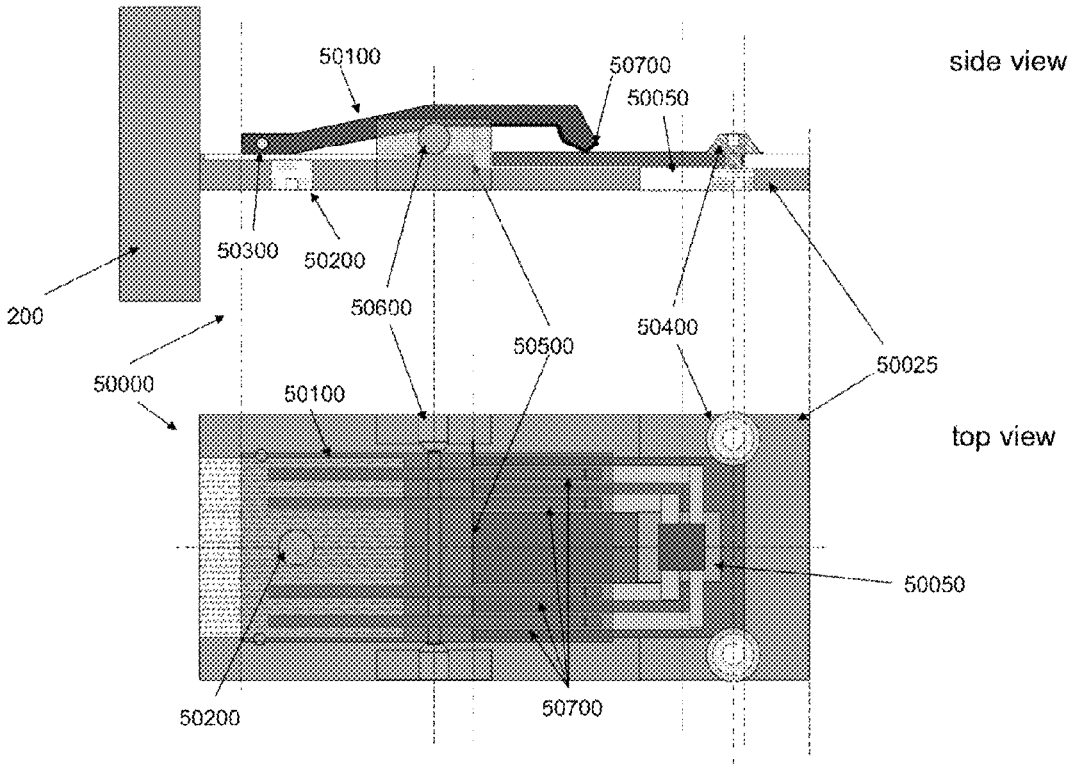
FIG. 5B shows a fourth embodiment of the tip region of a specimen holder described herein wherein the holder tip (50000) shows a flexing mechanism with a specimen support device, wherein the fulcrum is a one-piece fulcrum.

Yet another embodiment of the tip region of a specimen holder is shown in FIGS. 4A, 4B and 5A, 5B. FIGS. 4B and 5B show the tip region of a specimen holder of the present invention where the holder tip (50000) includes a flexible clamping mechanism in the resting state with a specimen support device loaded for use. FIGS. 4A and 5A show the tip region of the specimen holder of FIGS. 4B and 5B, respectively, where the holder tip (50000) is in a state ready for unloading a specimen support device. In all of these figures the flexible mechanism is comprised of a clip (50100) under which the device can be inserted, guide mechanism (50400), depth stop (50500), fulcrum (50600), fixed point (50300) and at least one electrical contact (50700). An optional set screw (50200) can be used to limit the distance that the clip can be flexed. The holder tip is comprised of a body (50025), a viewing region (50050) and a flexible clamping mechanism. The device is comprised of a frame (20000), electrical leads (20100), and a membrane region (20200). The difference between the 4A, 4B figures and the 5A, 5B figures is that in the former the fulcrum is a two-piece fulcrum and in the in latter the fulcrum is a one-piece fulcrum.

To mount the device under the clip (50100), the device is first oriented between the guide screws (50400) with the device's electrical leads (20100) oriented towards the slot. Downward pressure is then applied on the top surface of the clip (50100) at a point between the fulcrum (50600) and the fixed point (50300) resulting in the clip (50100) bending upward at the end near the guide mechanism (50400), such as guide screws, guide pins, or guide posts. With this pressure applied, the device is then inserted until the leading edge of the device meets the depth stop (50500). When the device is fully inserted against the depth stop (50500), the downward force on the clip (50100) is released which secures the device under the clip (50100) by friction during imaging and analysis. Simultaneous electrical contacts are formed between the electrical contacts (50700) underneath the clip (50100) and the electrical leads (20100) allowing electrical current to be passed from the electrical contacts (50700) to the electrical leads (20100). It should be appreciated by one skilled in the art that the electrical contacts of the specimen holder (50700) may extend from one length of the clip to the other or may be present in shorter sections so long as the electrical contacts are present for contact with the electrical leads of the device (20100).

Figure 6A:
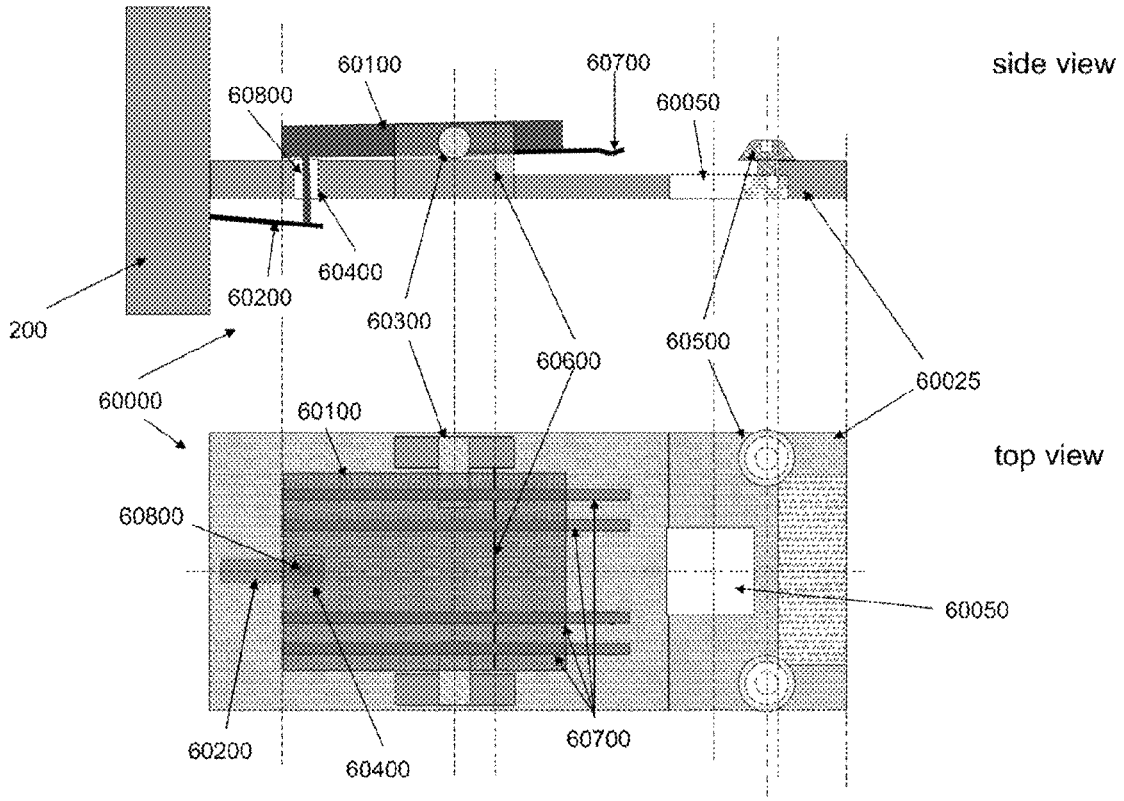
FIG. 6A shows a fifth embodiment of the tip region of a specimen holder described herein wherein the holder tip (60000) shows a clamping mechanism in an open state ready to receive a specimen support device.
Figure 6B:
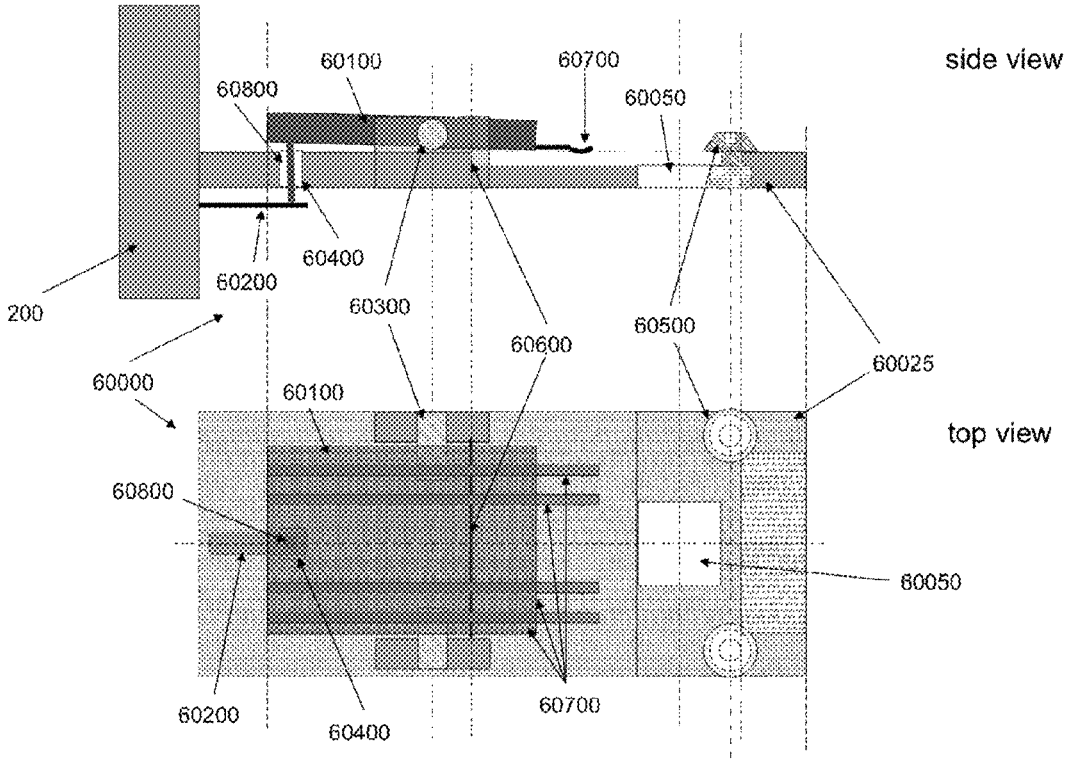
FIG. 6B shows a fifth embodiment of the tip region of a specimen holder described herein wherein the holder tip (60000) shows a clamping mechanism in a closed state without a specimen support device.
Figure 6C:
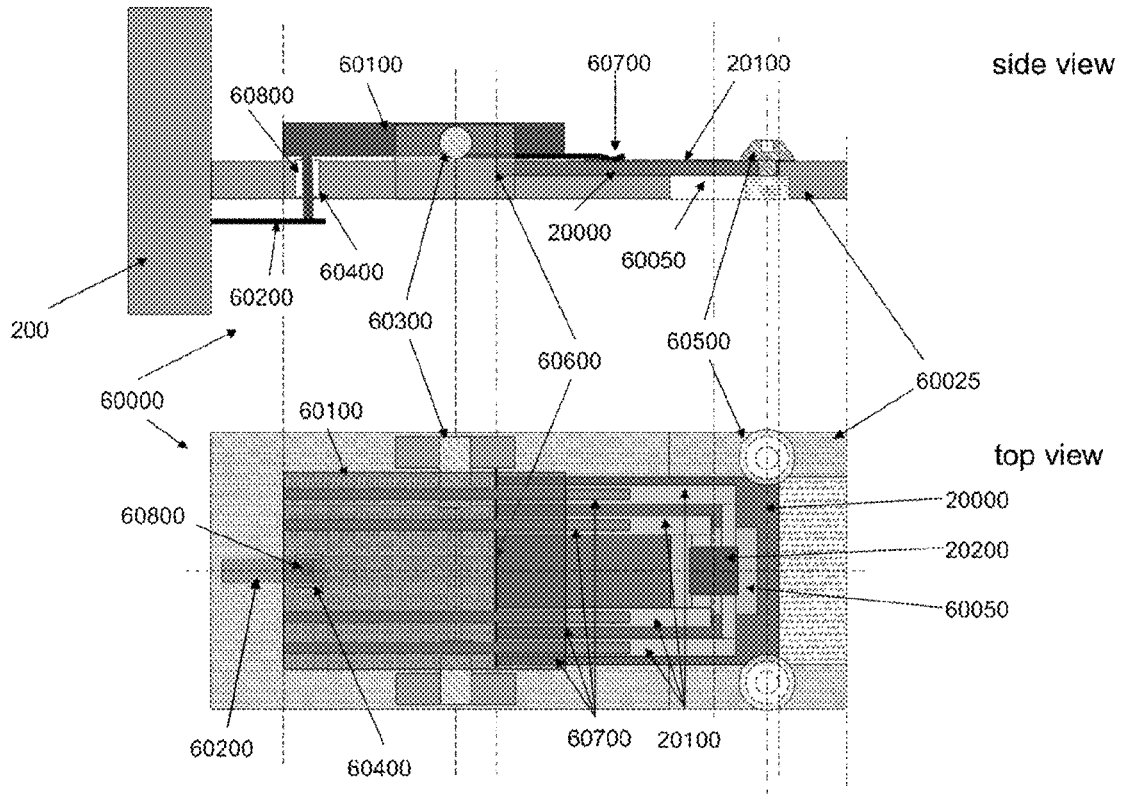
FIG. 6C shows a fifth embodiment of the tip region of a specimen holder described herein wherein the holder tip (60000) shows a clamping mechanism in a closed state with a specimen support device.

Another embodiment of the tip region of a specimen holder is shown in FIGS. 6A, 6B, and 6C. FIG. 6A shows the tip region of a specimen holder of the present invention where the holder tip (60000) includes a clamping mechanism in an open state ready to receive a specimen support device. FIG. 6B shows the tip region of the specimen holder of FIG. 6A where the holder tip (60000) is in a closed state without a specimen support device. FIG. 6C shows the tip region of the specimen holder of FIG. 6A where the holder tip (60000) is in a closed state with a specimen support device. In each of these figures, the clamping mechanism is comprised of a clip (60100), spring cantilever (60200), post (60800), post hole (60400), pivots (60300), guide mechanism (60500), depth stop (60600), and at least one electrical contact (60700). The post hole (60400) allows the post (60800) to contact and/or connect to both the spring cantilever (60200) and the clip (60100) through the holder tip (60000). The holder tip is comprised of a body (60025), a viewing region (60050), and the clamping mechanism. The electrical contact(s) preferably do not flex like a spring and will not be damaged from fatigue. In FIG. 6C a device is loaded into the tip and held in place by the clamping mechanism. The device is generally comprised of a frame (20000), electrical leads (20100), and a membrane region (20200).

In the clamping mechanism, the clip (60100) acts as a lever, the spring cantilever (60200) and post (60800) provide constant tension to the clip, the pivot (60300) allow the clip to pivot, and the guide mechanism (60500), such as guide screws, guide pins, or guide posts, provides lateral alignment to a device as it is loaded. When a device is completely loaded, the depth stop (60600) provides a means both to align the electrical contacts of the specimen holder (60700) to electrical leads of a device (20100) and to align the viewing region of the specimen holder tip (60050) with the membrane region of a device (20200). It should be appreciated by one skilled in the art that the electrical contacts of the specimen holder (60700) may extend from one length of the clip to the other or may be present in shorter sections so long as the electrical contacts are present for contact with the electrical leads of the device (20100). In addition the electrical contacts (60700) may consist of wires that protrude from the end of the clip, which make electrical contact to the electrical leads of the device (20100) using the bottom surface of the wire, or alternatively do not protrude from the end of the clip (see, e.g., FIG. 8 which illustrates the electrical contacts stopping at (or before) the end of the clip (60100).

The resting position for the clamping mechanism is shown in FIG. 6B where a spring cantilever (60200) pushes upward on a post (60800) through a post hole (60400), which pushes upward at one end of the clip (60100)), resulting in downward pressure created at the opposite end of the clip where the clip pivots at a set of pivots (60300) which may be smooth or threaded. The pivot is mounted to a mounting surface that is part of the body holder tip (60200).

To mount the device, downward pressure is placed on the spring end of the clip, which lifts the opposite end above the surface to a level at least as high as the thickness of the device, and typically higher, for example, greater than 1 mm (see FIG. 6A), although less than 1 mm is contemplated. The device is either placed in between the clip and the mounting surface manually, or slid underneath the clip along the mounting surface using the guide mechanism and depth stop as guidance. Once the device is in position, the pressure on the spring is released and the device is secured manually to the specimen tip (see FIG. 6C).

Electrical contacts from the holder to the device, typically in a range from 2 to 12 electrical contacts (60700 and 20100), may be provided by the conducting wires or paths and these electrical contacts may be positioned above, within, underneath and/or extended from the clip. These electrical contacts are electrically isolated from each other and from the clip itself (if the clip is made of a conductive material). When electrical pads exist on the device, the guide mechanism and depth stop will align the device with the clip to allow the electrical contacts from the clip and the pads from the device to contact one another when downward pressure on the clip is released. This will allow both mechanical pressure and electrical connections to be made in a novel, easy to operate design. The electrical contacts will be routed from the clip to the barrel, down the barrel to the end, and to a connector that exists at the specimen holder end that can be mated with a plug outside the microscope and connected to a power supply to provide voltage or current through the holder and interface to the specimen support device. Each conductor can remain isolated from each other as well as the three components that comprise the specimen holder.

Figure 7:
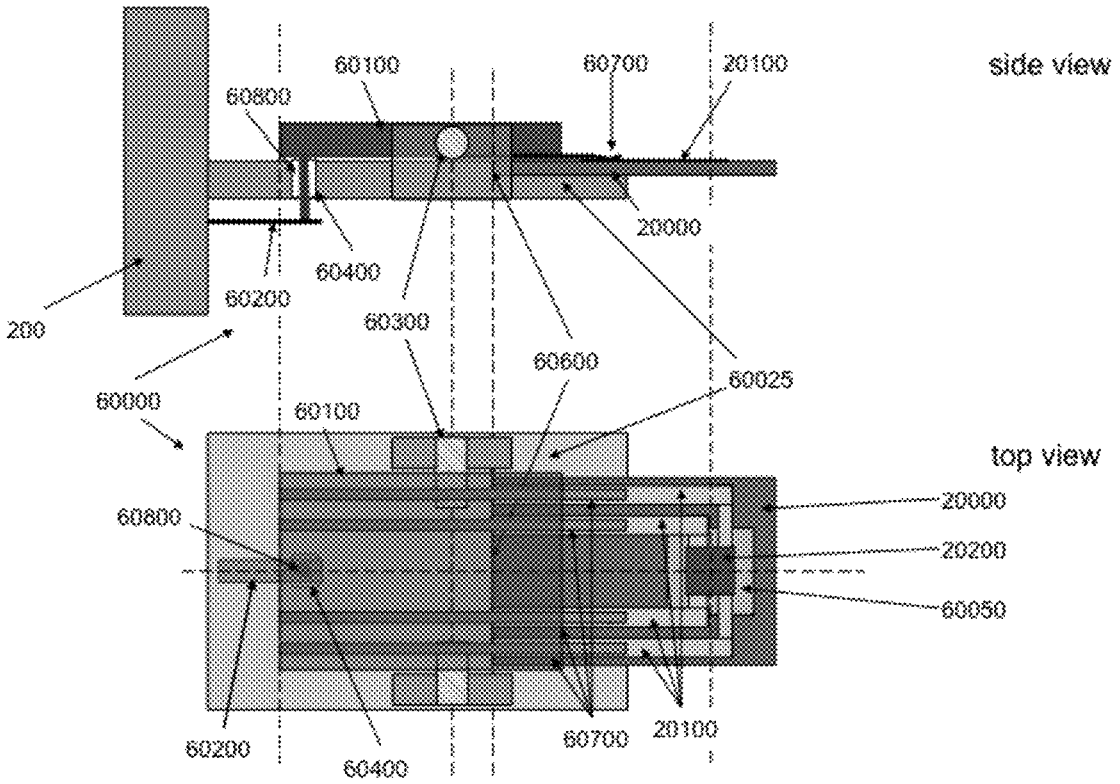
FIG. 7 shows an sixth embodiment of the tip region of a specimen holder described herein, wherein the holder tip (60000) shows a clamping mechanism in a closed state with a specimen support device.
Figure 8:
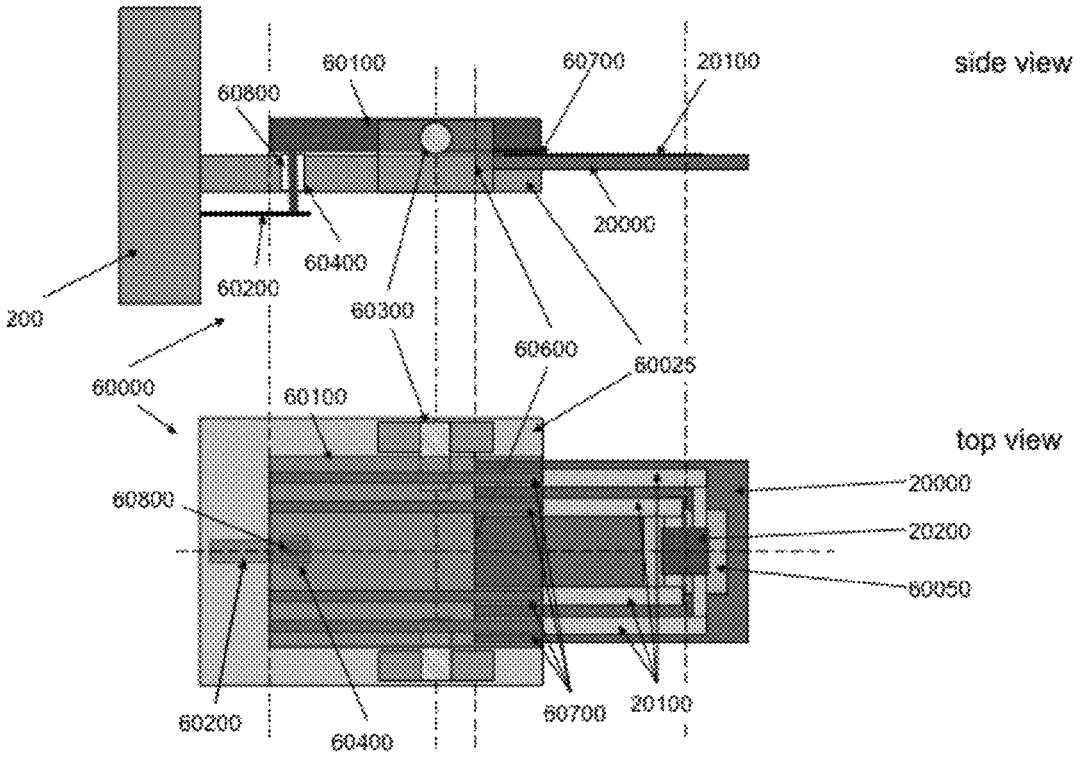
FIG. 8 shows an seventh embodiment of the tip region of a specimen holder described herein, wherein the holder tip (60000) shows a clamping mechanism in a closed state with a specimen support device.

Further embodiments of the tip region of the specimen holder are shown in FIGS. 7 and 8. FIG. 7 shows the tip region of a specimen holder similar to FIG. 6C, wherein the holder tip (60000) is in a closed state with a specimen support device, however, the mounting surface of the holder tip only extends about as far as the electrical contacts (60700) and as such, the holder tip does not include the viewing region of FIG. 6C. FIG. 8 also shows the tip region of a specimen holder similar to FIG. 6C, however, the electrical contacts do not extend beyond the end of the clip. Specifically, in FIGS. 7 and 8, the clamping mechanism is comprised of a clip (60100), spring cantilever (60200), post (60800), post hole (60400), pivots (60300), depth stop (60600), and at least one electrical contact (60700). The post hole (60400) allows the post (60800) to contact and/or connect to both the spring cantilever (60200) and the clip (60100) through the holder tip (60000). The electrical contact(s) preferably do not flex like a spring and will not be damaged from fatigue. The holder tip is comprised of a body (60025) and the clamping mechanism. In FIG. 7, the body (60025) extends just to the edge of the electrical contacts (60700) and the specimen support device (20000) cantilevers beyond the body (60025). In FIG. 8, the electrical contacts (60700) do not extend beyond the end of the clip (60100) and the body (60025) is illustrated to extend as far as the edge of the clip (60100), wherein the specimen support device (20000) cantilevers beyond the body (60025). The embodiments in FIGS. 7 and 8 allow a rigid specimen support to extend beyond the body (60025) and still maintain mechanical contact with the body (60025) and electrical contact with the clip (60100) through the electrical contacts (60700).

FIG. 7 and FIG. 8 are based upon the embodiment illustrated in FIGS. 6A, 6B and 6C, but may also be applied to the embodiments shown in FIGS. 2A, 2B, 2C, 3A, 3B, 3C, 4A, 4B, 5A and 5B, whereby the mounting surface of the holder tip only extends about as far as the electrical contacts and as such, the holder tip does not include the viewing region.

The advantages of the specimen holder described herein include, but are not limited to: the ready adaptation of the specimen holder to accommodate specimen support devices having varying shapes and sizes without the need to machine frames and custom parts to align different device geometries; providing a simple method for mounting and exchanging devices and making electrical contacts to devices without the need for partially disassembling the specimen tip; allowing for interchangeable specimen tips to accommodate different specimen supports or to be used with different barrels and ends; and eliminating the use of a delicate spring contact finger. For example, the electrical contacts of the present invention may be effectuated at one of the clip (see, e.g., FIGS. 2-8) whereby there is no spring present at all or the spring is distally positioned at the other end of the clip.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

What is claimed is:

1. An electron microscope specimen holder comprising a body, a clipping means, a spring, a viewing region, and at least one guide mechanism, wherein the clipping means comprise an article of manufacture having a top surface, a bottom surface, a first end, a securing means, a second end, and at least one electrical contact integrated on and/or in the bottom surface of the article, and wherein the spring is in contact with the bottom surface of the second end of the article and, provides constant force to displace the first end of the article, and, wherein the securing means are positioned between the first end and the second end of the article.

2. The specimen holder of claim 1, wherein the securing means comprise a pivot positioned between the first end and the second end of the article.

3. The specimen holder of claim 1, wherein the [second] *first* end of the article is pivotally raised by applying downward pressure to the top surface of the [first] *second* end of the article for insertion of a specimen support device between the bottom surface of the [second] *first* end of the article and a top surface of the body.

4. The specimen holder of claim 1, wherein the article is pivotally lowered such that at least one electrical lead of a specimen support device substantially contacts at least one electrical contact of the article.

5. The specimen holder of claim 1, wherein the at least one electrical contact extends from the second end of the article, terminates at the second end of the article, or terminates before the second end of the article.

6. The specimen holder of claim 1, wherein the at least one electrical contact of the clipping means extends from the clipping means to a barrel, from the barrel to an end, and onto an electrical connector.

7. The specimen holder of claim 1, wherein the specimen holder is inserted into an electron microscope.

8. The specimen holder of claim 1, further comprising a specimen support device mechanically secured between the clipping means and the body.

9. The specimen holder of claim 8, wherein the specimen support device comprises a frame, at least one electrical lead and at least one membrane region.

10. The specimen holder of claim 8, wherein the specimen support device is aligned using a depth stop and [optionally,] at least one additional guide mechanism, such that at least one electrical lead of the specimen support device substantially contacts at least one electrical contact of the article.

11. The specimen holder of claim [1] *9*, wherein the specimen support device is aligned using [the] *a* depth stop and [optionally,] at least one additional guide mechanism, such that the viewing region and the at least one membrane region of the specimen support device substantially correspond.

12. The specimen holder of claim [1] *10*, wherein the at least one additional guide mechanism comprises guide screws.

13. A method of using a specimen holder in electron microscopy, said method comprising:

positioning a specimen support device in the specimen holder of claims 1; and inserting said specimen holder in an electron microscope.

14. The method of claim 13, wherein a specimen is on the specimen support device and an electron beam is controlled to form an image of the specimen.

15. The specimen holder of claim 1, wherein the guide mechanism provides lateral alignment to a device as it is loaded.

16. The specimen holder of claim [1] *8*, wherein the spring is any object that has a spring constant (k) and exerts a force onto [a] *the* specimen support device.

17. The specimen holder of claim 1, wherein the at least one guide mechanism is positioned on a top surface of the body.

18. The specimen holder of claim 1, further comprising a set screw which prevents the spring from being overcompressed when a device is loaded into the specimen holder.

19. A method of providing an electrical contact between a specimen and a specimen holder of an electron microscope, said method comprising: positioning a specimen on a specimen support device, wherein the specimen support device comprises a frame, at least one electrical lead and at least one membrane region; and inserting the specimen support device in a specimen holder, wherein the specimen holder comprises a body, a clipping means, a spring, a viewing region, and at least one guide mechanism, wherein the clipping means comprise an article of manufacture having a top surface, a bottom surface, a first end, a securing means, a second end, and at least one electrical contact integrated on and/or in a bottom surface of the article, wherein the spring is in contact with the bottom surface of the second end of the article and, provides constant force to displace the first end of the article; wherein the securing means are positioned between the first end and the second end of the article; and wherein at least one electrical lead of the device substantially contacts at least one electrical contact of the clipping means.

* * * * *